United States Patent
Yamamoto et al.

(10) Patent No.: US 6,723,047 B1
(45) Date of Patent: Apr. 20, 2004

(54) VOLITION INDUCTION APPARATUS AND INPUT/OUTPUT APPARATUS WHICH USE OPTICAL MEASURING INSTRUMENT, AND RECORDING MEDIUM

(75) Inventors: Tsuyoshi Yamamoto, Kawagoe (JP); Atsushi Maki, Fuchu (JP); Yoshitoshi Ito, Ome (JP); Yuichi Yamashita, Kawagoe (JP); Hideaki Koizumi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/009,187
(22) PCT Filed: Jun. 9, 1999
(86) PCT No.: PCT/JP99/03075
§ 371 (c)(1), (2), (4) Date: Dec. 7, 2001
(87) PCT Pub. No.: WO00/74572
PCT Pub. Date: Dec. 14, 2000

(51) Int. Cl.⁷ .............. A61B 5/00; A61B 10/00
(52) U.S. Cl. ............. 600/309; 600/504; 128/905; 463/36; 340/825.19
(58) Field of Search ................... 600/310, 322, 600/323, 544, 545; 128/905, 920, 923; 463/36; 482/4–9, 901, 902; 434/29; 340/573.1, 825.19

(56) References Cited

U.S. PATENT DOCUMENTS

| | | | |
|---|---|---|---|
| 4,859,057 A | * | 8/1989 | Taylor et al. ............... 600/323 |
| 5,779,631 A | * | 7/1998 | Chance ...................... 600/473 |
| 5,983,129 A | * | 11/1999 | Cowan et al. .............. 128/905 |
| 5,995,857 A | * | 11/1999 | Toomim et al. ............ 600/322 |
| 6,018,673 A | * | 1/2000 | Chin et al. .................. 600/322 |
| 6,215,403 B1 | * | 4/2001 | Chan et al. ................. 600/323 |
| 6,240,309 B1 | * | 5/2001 | Yamashita et al. .......... 600/407 |

FOREIGN PATENT DOCUMENTS

| | | |
|---|---|---|
| JP | 9-98972 | 4/1997 |
| JP | 9-135825 | 5/1997 |
| JP | 9-149894 | 6/1997 |

* cited by examiner

*Primary Examiner*—Eric F. Winakur
*Assistant Examiner*—David J. McCrosky
(74) *Attorney, Agent, or Firm*—Mattingly, Stanger & Malur, P.C.

(57) ABSTRACT

It has long been unclear in what degree the brain should be activated and how much the blood volume should be varied for controlling a signal by measuring the concentration of metabolic substance in the tissue or change of concentration thereof using the light and by using the result of measurement. The present invention provides an optical measuring system which can present the concentration of metabolic substance in the tissue which may be detected with a subject by itself or the target value of change of the concentration. Thereby, it is now possible for the subject by itself to more easily detect and control the concentration of metabolic substance in the tissue or change of concentration thereof. As a result, cerebral information can be extracted in direct to realize various applications such as control of the game machines and welfare facilities.

2 Claims, 22 Drawing Sheets

31

32

VOLITION INDUCTION APPARATUS AND INPUT/OUTPUT APPARATUS WHICH USE OPTICAL MEASURING INSTRUMENT, AND RECORDING MEDIUM

BACKGROUND OF THE INVENTION

The present invention relates to an apparatus for controlling signals coming from tissue by utilizing an apparatus for measuring concentration of metabolic substance in the tissue or change of concentration thereof based on a light signal.

An apparatus for measuring changes of characteristics of subjects utilizing an optical measuring instrument has been disclosed in JP-A No. H9-98972 and moreover an apparatus for issuing an alarm if any change exceeding the predetermined value is generated as a result of monitoring the conditions of the subject has also been disclosed in JP-A No. H9-149894.

An existing apparatus for acquiring signals from the tissue has been structured to irradiate the tissue in the body as an measurement object with a probe light in the wavelength reacting to such tissue, to detect change of probe light having passed the living body and transmit a certain signal when such change has exceeded the predetermined value. However, any structure to support the volition of living body is not disclosed in these references.

This measuring instrument includes an optical element to be loaded on the skin of a living body, which is represented by an optical fiber as a light source and a light detector. However, if the loading area is selected at the head portion, such optical element must be loaded on the scalp by parting the hair of head. Therefore, the structure for loading an optical element on the scalp has been required.

SUMMARY OF THE INVENTION

In the present invention, following two means are provided. The first means is an apparatus having the structure for displaying a signal level obtained from a subject and the signal level to be obtained on a display to induce the volition of the subject, or notifying such levels to the subject in terms of a sound and detecting a change of subject based on such sound to notify again this change to the subject, and moreover feeding back the signal obtained to a living body as the subject to assist induction of volition of the body until the target value can be attained.

The second means includes a light source and a light detector provided by the present invention which can easily implement radiation of light and detection thereof. In the present invention, a light source for radiation and a sensor for detection must be loaded on the scalp. In the existing cerebral function measuring method, fitting of a sensor which is a general name of such elements is very complicated and it has been conducted by only an authorized person represented by an inspection engineer. However, it has been requested to develop an easier sensor loading method for the spreading of the measuring method. The present invention provides, by paying attention to a hair fixing tool (probe) represented as a hair band, a Katyusha or a hair pin which may be available in the market, an element, comprising, within such hair fixing tool (probe), a light source for irradiating a living body with the light and a sensor for detecting the light having propagated a living body, which may be handled easily and can also be loaded to the heads of many peoples.

DETAILED DESCRIPTION OF THE PREFERRED EMBODIMENTS

Figure 1:
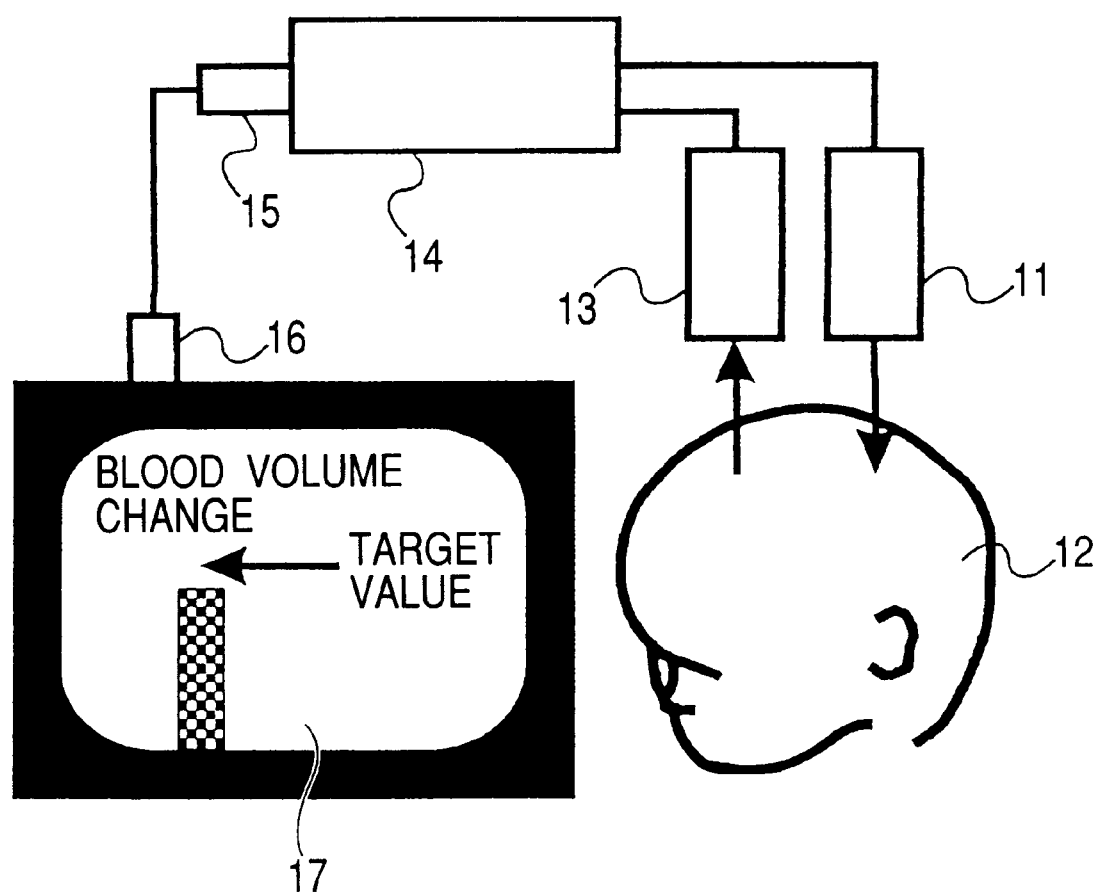
FIG. 1 shows the basic structure of a volition induction apparatus and an input/output apparatus using an optical measuring instrument and a recording medium based on the present invention.

Embodiment 1:

FIG. 1 shows the basic structure of a measuring method as an embodiment of the present invention. Numeral 11 denotes a light source used for the measurement. This light source is in contact with the skin of the subject 12. The light source 11 is composed of a light source represented by a semiconductor laser, gas laser, free electron laser, lamp, fluorescent lamp and light emitting diode and an optical wave guide represented by an optical fiber. However, the light source using a light source element represented by a semiconductor laser, gas laser, free electron laser, lamp and light emitting diode may also be placed in contact with the subject. Numeral 13 denotes a light detector using an element represented by a photodiode or a photomultiplier which can detect the light propagated within a living body.

Here, it is also possible to introduce the structure that a light detector represented with these elements may be allocated on the skin of the subject or the structure that an optical wave guide is provided between the skin of the subject and light detector using an optical guiding means like the light source 11. The light source 11 and light detector 13 are connected to a signal processor 14. The structure of this signal processor 14 will be explained later. The detected signal intensity is transmitted to a display 17 via a signal output connector 15 and a signal input connector 16. This display has a function to display both intensity of detected light and its target value. This target value may be set freely to the desired value using the signal processor (14). Moreover, the intensity of detected light and its target value shown in the figure may be displayed on the same display or on different displays.

Figure 2:
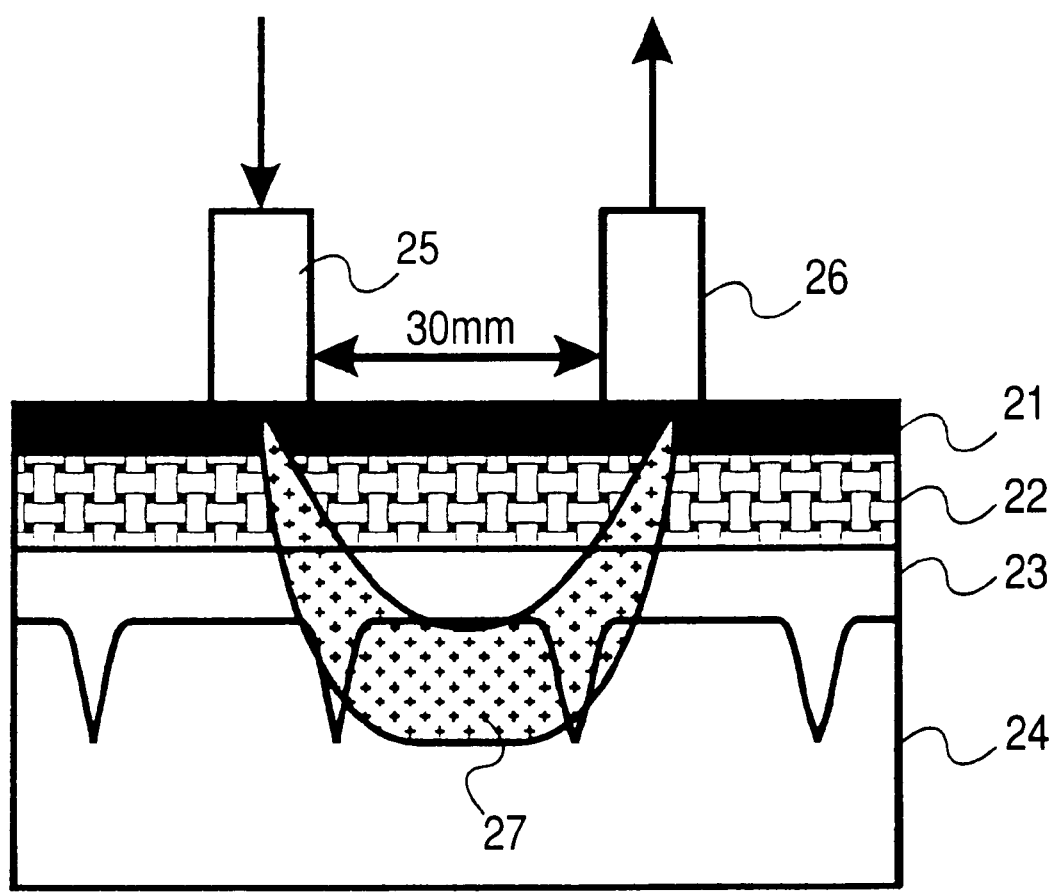
FIG. 2 shows a propagation path of light within a living body.

FIG. 2 shows an internal structure of a head and its right propagation route. The structure of brain is composed, from the upper part of the skin, of the scalp (21), a skull (22), a cerebrospinal fluid (23) and a cerebral cortex (24) or the like. There exits personal change in the thickness of this structure. In the case of an adult, the cerebral cortex exists at the internal side of the skull in the depth of about 15 mm from the scalp. The light irradiated from the light source 25 is scattered with tissue in the body. The light used for the measurement is the near infrared light having higher permeability for the tissue. In the case where the light detector 26 is allocated at the area isolated by about 30 mm from the light source 25, the light reaching the light detector 26 is propagated through the cerebral cortex (light propagation route: 27). This cerebral cortex is tissue to which the high-order cerebral functions represented by exercise, sense and language are concentrated. Therefore, a blood volume of this tissue increases or decreases depending on the activity of brain. The near infrared light to be used for the measurement is absorbed with hemoglobin and thereby intensity of the light having reached the light detector 26 increases or decreases also depending on the activity of brain.

Figure 3:
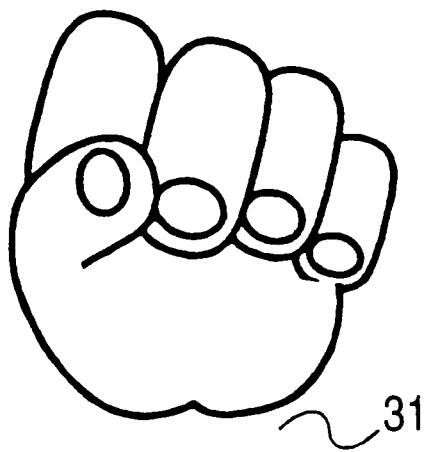
FIG. 3 shows an example of a task which can activate the functions of the brain and change the intensity of light to be detected.
Figure 3:
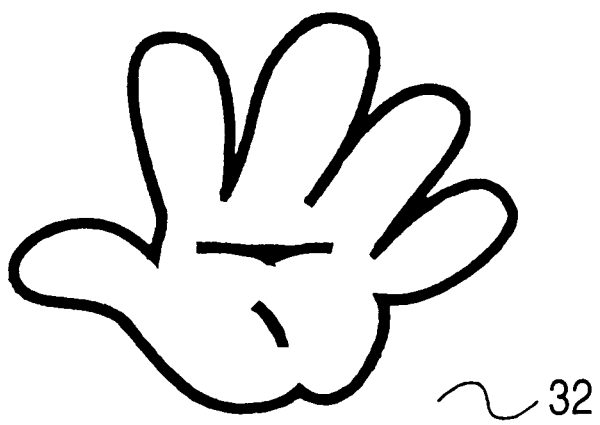

FIG. 3 shows an example of a task which can activate the functions of brain to change the intensity of detected light. In FIG. 3, the right hand is in the condition of gripping (31) while the right hand is in the condition of palm (32). Both right and left hands are alternately set to these conditions repeatedly. Namely, the right and left hands are alternately set to the conditions of gripping and palm. With introduction of this task, man motor area which controls the functions of fingers of a man can be activated.

Figure 4:
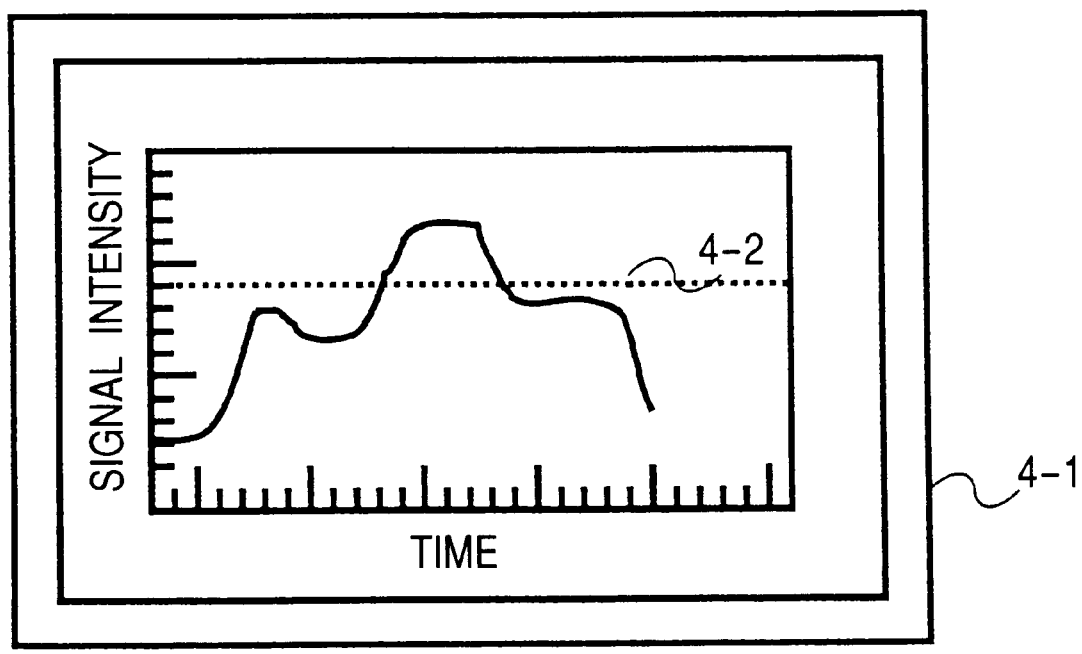
FIG. 4 shows a result of evaluation for dependence on time of intensity change of the light having propagated the brain.

FIG. 4 shows dependence on time of intensity of the light propagated in the brain with the method shown in FIG. 1, FIG. 2 and FIG. 3. After the start of measurement, the finger motions of hand in gripping and the palm of hand shown in FIG. 3 have been executed. Moreover, the light source (11) and light detector (13) shown in FIG. 1 have been allocated on the scalp on the subject with an interval of 30 mm. On the display (41), a display image which can display the dependence on time of signal intensity is displayed. Moreover, on this display image, the "target value" (42) of signal intensity change is set (in FIG. 4, indicated with a broken line). A subject person executes, after the start of measurement, the exercises based on the volition to attain this target value and executes the exercises to achieve this "target value". In this embodiment, since blood volume within the brain and the target value of change thereof are indicated obviously, it becomes apparent with how many times the exercise of fingers for gripping and palm of hands should be repeated to obtain the target value. Namely, change of blood volume in the brain is processed as a signal intensity with a probe using the light source (11) and light detector (13). The subject person observes this result. If the result does not reach the target value, the subject person raises the blood volume in the brain by intensifying the volition until the target value can be attained. Use of the measuring system which can induce such volition enables detection of change by the subject person in the detected blood volume depending on change of blood volume resulting from activity of the brain and thereby it becomes easier for the subject person to transfer the volition thereof.

Figure 5:
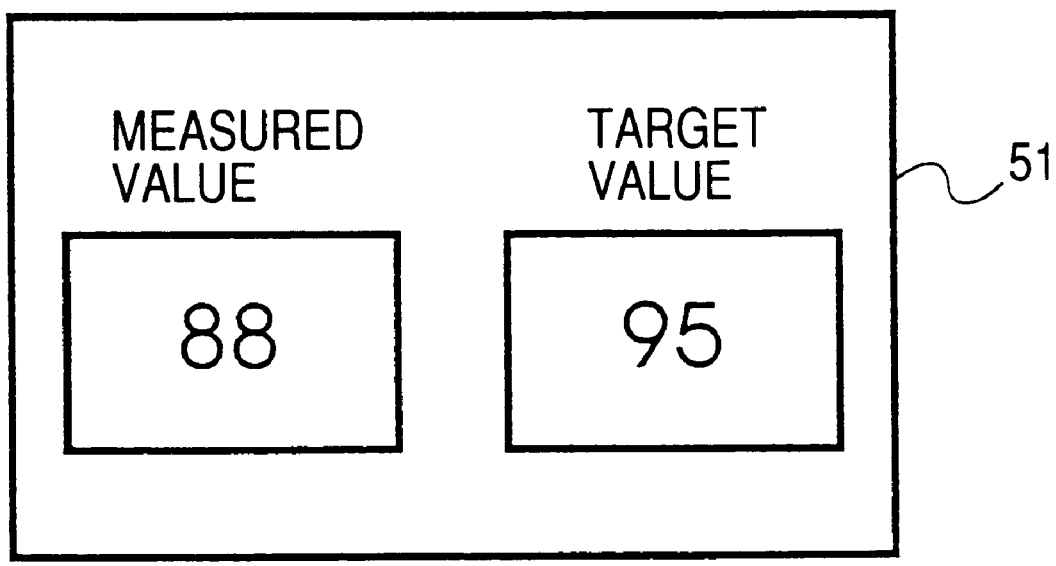
FIG. 5 shows a method of setting the visual target value.
Figure 5:
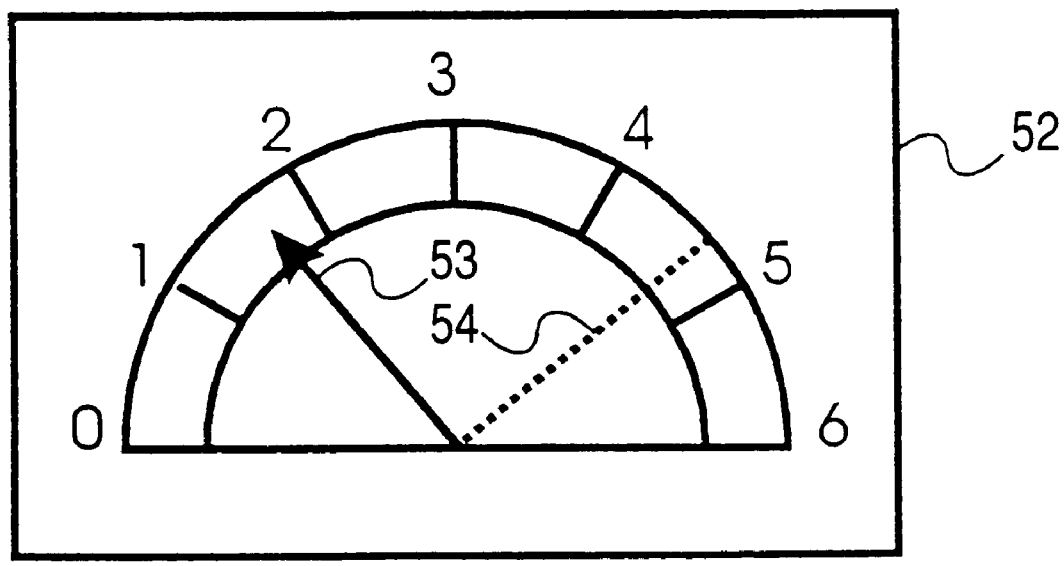

Embodiment 2:

FIG. 5 shows a method of setting a visible target value based on the embodiment 1 of the present invention. Numeral 51 denotes a digitized method. Both measured value and target value are displayed by the digitized method. A value ("88" in the digitized method) displayed as the measured value sequentially changes after the start of measurement. Meanwhile, the target value is set before the start of measurement and the equal value is displayed during the measurement. In the digitized method 51, the target value "95" is displayed (the method to show the measured value and target value like the speed meter is indicated in the method 52). Numeral 53 denotes a pointer which can display the measured value indicated in the digitized method 51. Meanwhile, the numeral 54 denotes a pointer which can indicate the target value indicated in the digitized method 51. These measured value and target value may be displayed with a meter using a pointer (a pointer mechanically moves in actual using a motor) or may be displayed with a meter using computer graphics.

Figure 6:
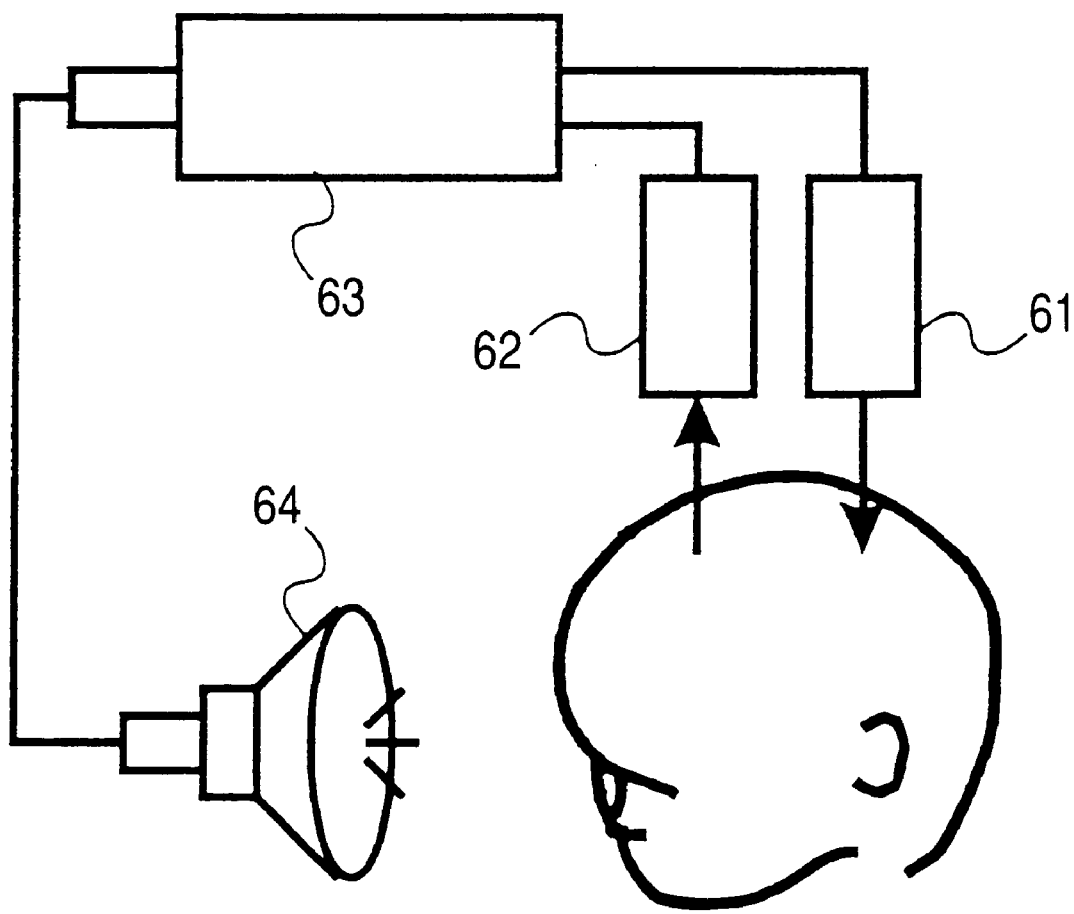
FIG. 6 shows a measuring system ①which can stimulate auditory sense of a man using a sound wave.

FIG. 6 shows a measuring system which can stimulate the auditory sense of man using a sound wave. A living body is irradiated with the light using a light source 61 and a light detector 62 to detect intensity of light propagated through a living body. Like the embodiment of FIG. 1, the detected signal is processed with a signal processor 63. Difference between the embodiment of FIG. 1 and this embodiment 3 is that a sound wave generator 64 which can generate sound wave depending on the intensity of detected light (a speaker, in this case) is provided. This embodiment enables transfer of volition by detecting increase or decrease of blood volume in the brain even in the subject or body having a handicap in the auditory sense.

Figure 7:
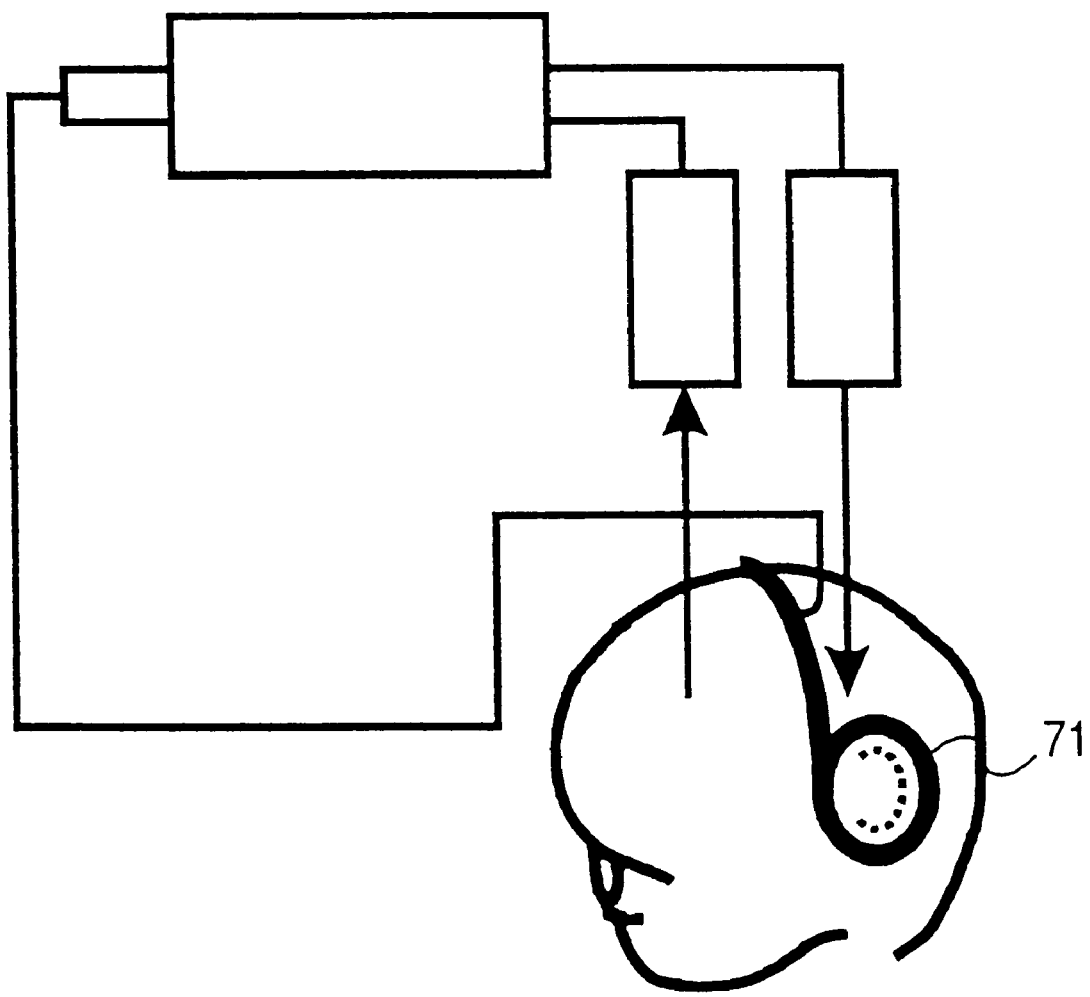
FIG. 7 shows a measuring system ②which can stimulate auditory sense of a man using a sound wave.

Embodiment 3:

FIG. 7 shows an example of a modification of the method of FIG. 6. In this embodiment, a pair of headphones are used as a sound wave generating means. In the embodiment shown in FIG. 6, it is impossible in some cases that the subject cannot accurately hear the sound wave depending on increase and decrease of blood volume in the brain, for example, when ambient noise level is high. In this embodiment, the ambient noise level can be shielded by using a pair of headphones.

Figure 8:
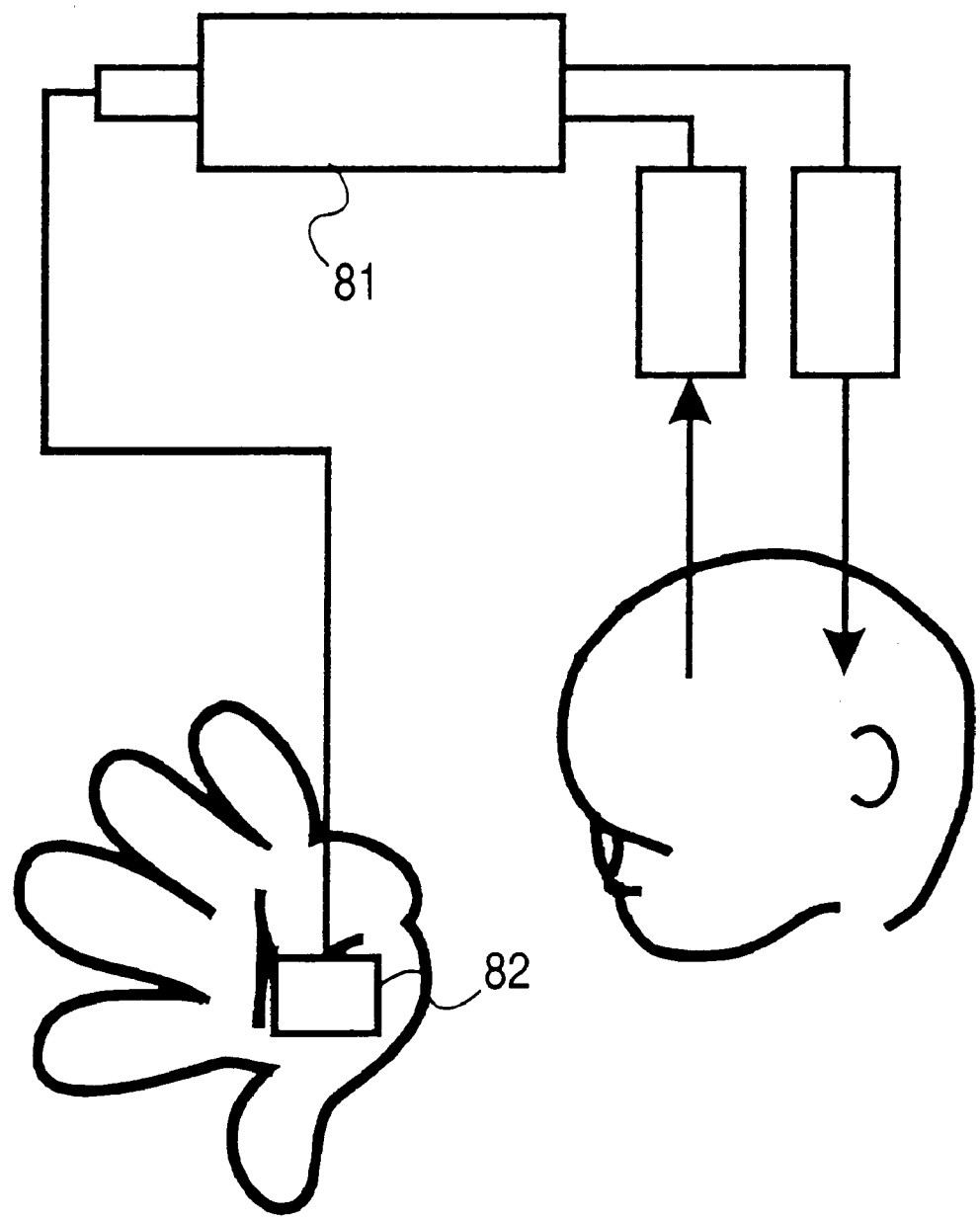
FIG. 8 shows a method for presenting change of blood volume within the brain to a subject using a vibrator.

FIG. 8 shows a method of presenting, to the subject, a change of blood volume in the brain using a vibrator as the sound wave generating means. The vibrator 82 is controlled using detected light intensity having reached the signal processor 81. The vibrator may be placed in contact with the desired area on the subject. Use of this embodiment will stimulate the sense of touch of the living body.

Figure 9:
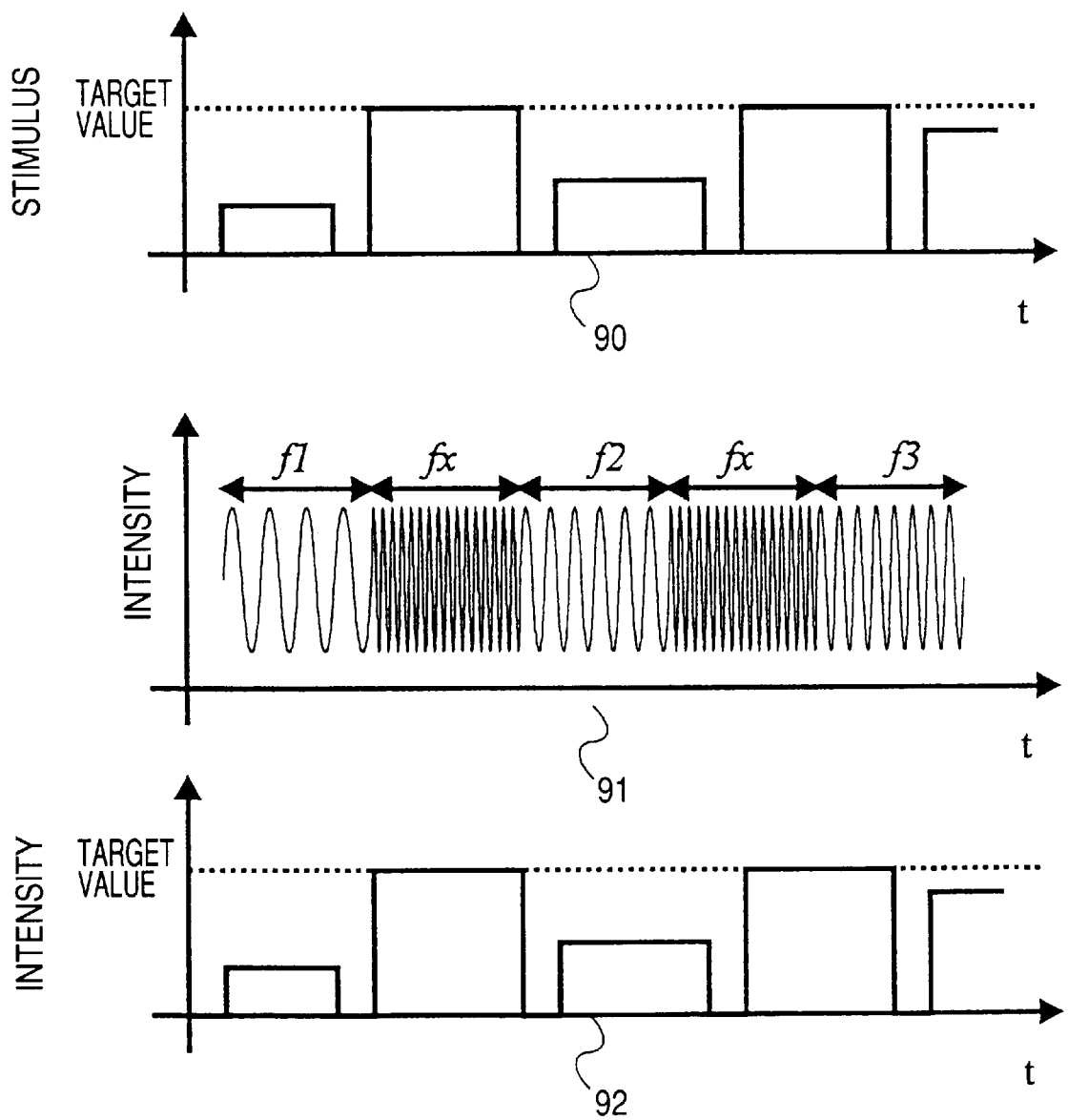
FIG. 9 shows a stimulating method of sound wave equivalent to the detected light intensity and a stimulating method of sound wave equivalent to the target value in a sound wave generating method.

FIG. 9 shows a method of stimulation with sound wave equivalent to intensity of the detected light and a method of stimulation with sound wave corresponding to the target value in the sound wave generating method shown in FIG. 6, FIG. 7 and FIG. 8. Numeral 90 denotes the stimulation frequency depending on the time when the sound wave is applied to the subject by modulating the frequency of the sound wave. Symbols f1, f2, f3 shown in 91 denote the frequency equivalent to the signal intensity and have a constant correlation. Meanwhile, fx denotes the frequency corresponding to the target value. These frequencies are applied to the subject in the constant interval to generate the sound wave. The subject changes the blood volume in the brain to approximate f1, f2, f3 to fx, for example, depending on the task sequence shown in FIG. 3. On the other hand, numeral 92 denotes a method for changing intensity of sound wave depending on the intensity of detected light. The subject can detect a degree of attaining the target value by alternately changing the intensity of the sound wave equivalent to the measured value and that of the sound wave equivalent to the target value.

Figure 10:
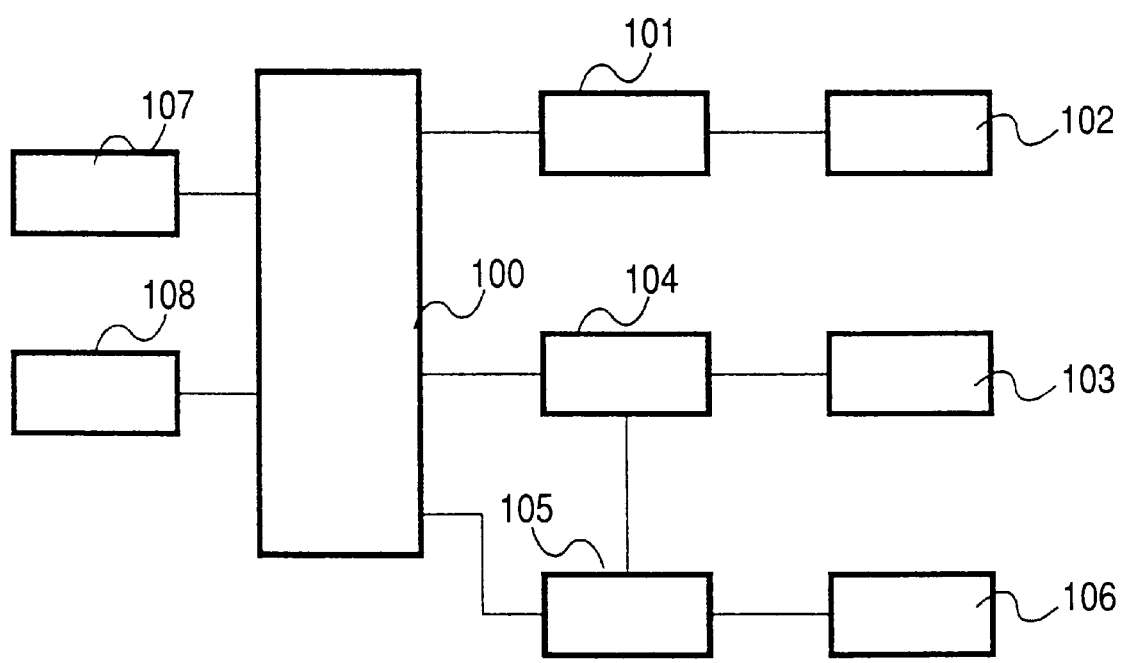
FIG. 10 shows a block diagram of an embodiment of the internal structure of a signal processing system 14.

FIG. 10 shows an embodiment of the internal structure of the signal processing system 14 in the measuring system shown in FIG. 1. The numeral 100 denotes a central processing unit (CPU). Numeral 101 denotes an illumination intensity controller. As an example, a pulse laser intensity controller and a continuous wave (CW) intensity controller may be listed. The numeral 102 denotes a connector to the light source; 103, a connector to the light detector; 104, an electronic circuit represented by a filter, lock-in amplifier, operational amplifier, analog/digital converter (A/D converter) for processing an electric signal thereof. The processed signal is processed to an image signal with an image processor 105 and is then outputted from a terminal 106. Numerals 107, 108 are fixed disk and memory, respectively. These elements are connected by wire or by radio with the central processing unit CPU 100. The information, for example, represented by the following examples can be stored temporarily or permanently by connecting these fixed disc and memory. In regard to the information related to the light source, a light volume of the light source, pulse width of pulse laser and interval of oscillation can be listed. Next, as the information related to the detected light intensity, the intensity and time of the light propagated through the tissue of a living body may be listed. Next, in regard to the image signal using the image processor 105, intensity and time of the signal displayed on the display and the target value to be set on the display image may be listed. The fixed discs 107, 108 and the information stored in the memory are not restricted to the parameters explained above.

Figure 11:
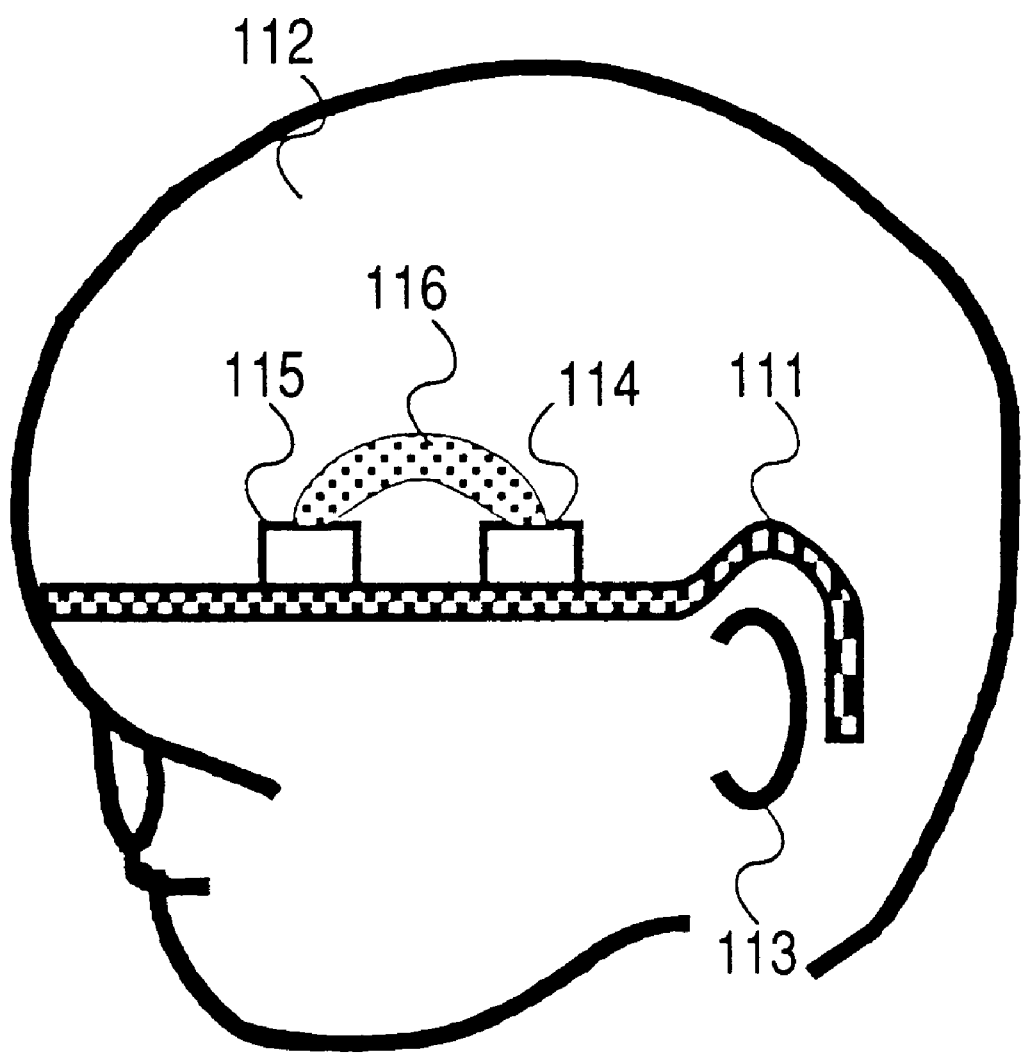
FIG. 11 shows a method of irradiating a subject with the light.

Embodiment 4:

FIG. 11 shows an example where a probe (111) whose shape resembles a frame of glasses. The probe is fixed with an ear of the subject (112). At the surface of probe, a pair of light source (114) and light detector (115) or more are allocated. The light propagation route (116) within a living body of the light emitted from the light source to reach the light detector is shown in the figure.

Figure 12:
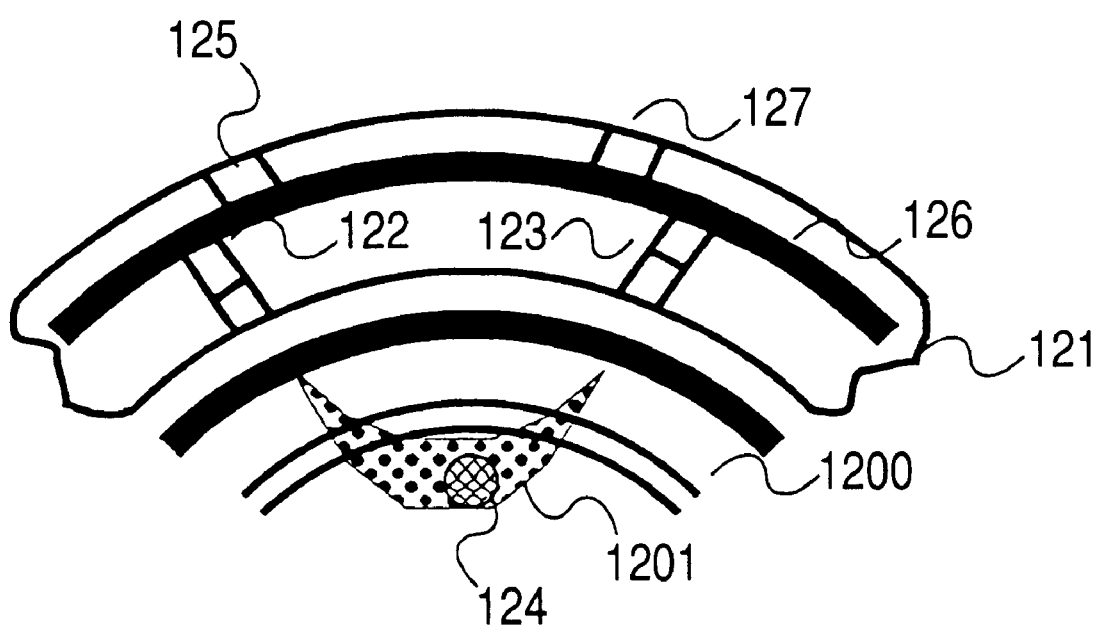
FIG. 12 shows an embodiment of the internal structure of a probe shown in FIG. 11.

FIG. 12 shows an embodiment of the internal structure of this probe. The surface of a living body is generally formed of the curving surface and the shape thereof is different to a large extent depending on individuals. Therefore, the probe is required to have the structure enabling the loading to peoples as many as possible. The probe used in this embodiment is all formed of a flexible material. The probe (121) is formed of a resin material represented by rubber and plastic. A light source (122) and a light detector (123) are embedded within this probe. The probe, light source and light detector are allocated in the proximity of the localized area (124) to change the blood volume. The power source (125) used to drive the light source is also embedded in this probe. The profile of this power source maybe selected freely as required. For example, the power source may be of the type allowing exchange thereof when the power is consumed such as a dry-battery or a button-battery. Otherwise, it may be of the type which is driven through conversion of external energy represented by a solar battery. These power source and light source may be coupled with a flexible electric device (126). The light detected with the light detector (123) is converted to an electric signal depending on the intensity thereof. This electric signal is detected with an optical fiber in the case of the embodiment shown in FIG. 1. Here, a method using the electromagnetic wave shown in FIG. 12 may also be listed other than the method shown in this embodiment. In this embodiment, an antenna (127) is also embedded within the probe. Use of this method will eliminate an optical fiber shown in FIG. 1 and thereby the subject may move within the range wherein a radio signal can be received. Therefore, the measuring condition is more profitable. The number of pairs of the illuminating points and detecting points in the present embodiment is only one (1). The number of pairs of the illuminating point and detecting point can be set freely other than that (one) of this embodiment.

Figure 13:
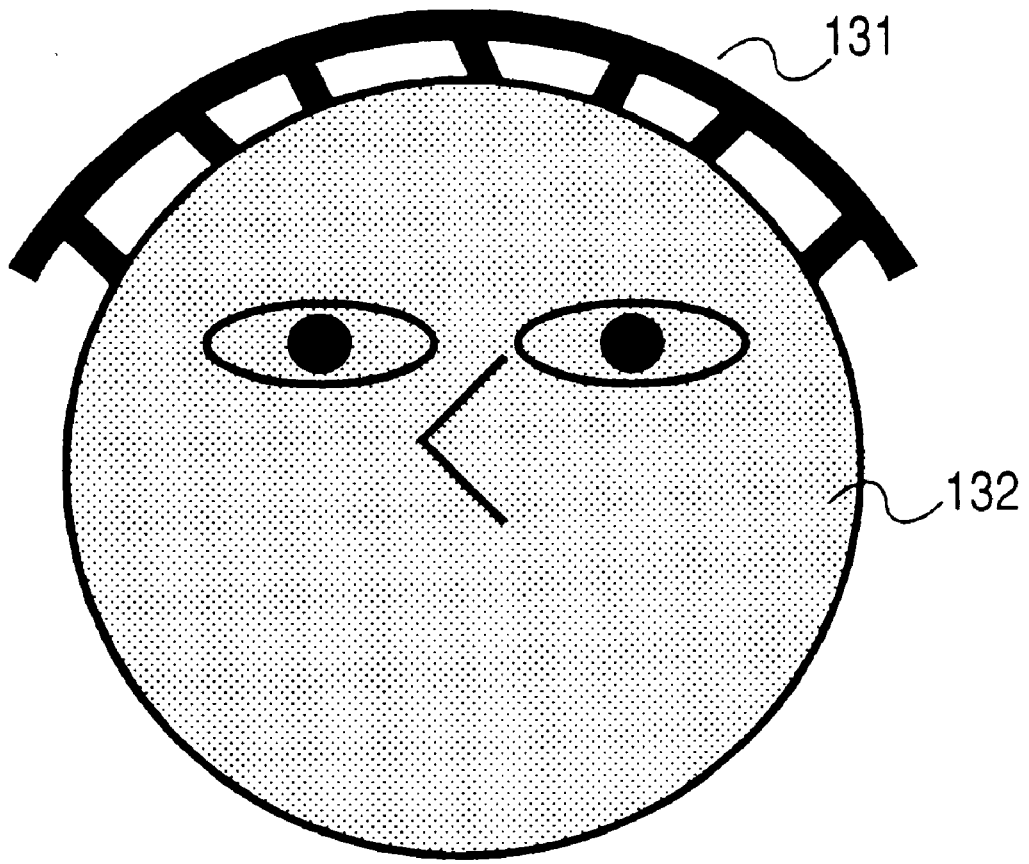
FIG. 13 shows an embodiment in the case where "Katyusha" is used as the probe.

Embodiment 5:

FIG. 13 shows an embodiment in which the "Katyusha" (131) is used as the probe. The "Katyusha" is a tool used in general with a woman to order the hair. The "Katyusha" is generally provided with a projected area at the surface of resin. Therefore, when the "Katyusha" is loaded, the projected area is placed in contact in direct with the scalp of the subject (132). On the occasion of irradiating the tissue of body with the light, the light is absorbed with the hair and thereby the light illumination efficiency and detection efficiency are often lowered. According to this embodiment, however, the light can be illuminated and detected efficiently by using the "Katyusha" even when the subject has sufficient hair.

Figure 14:
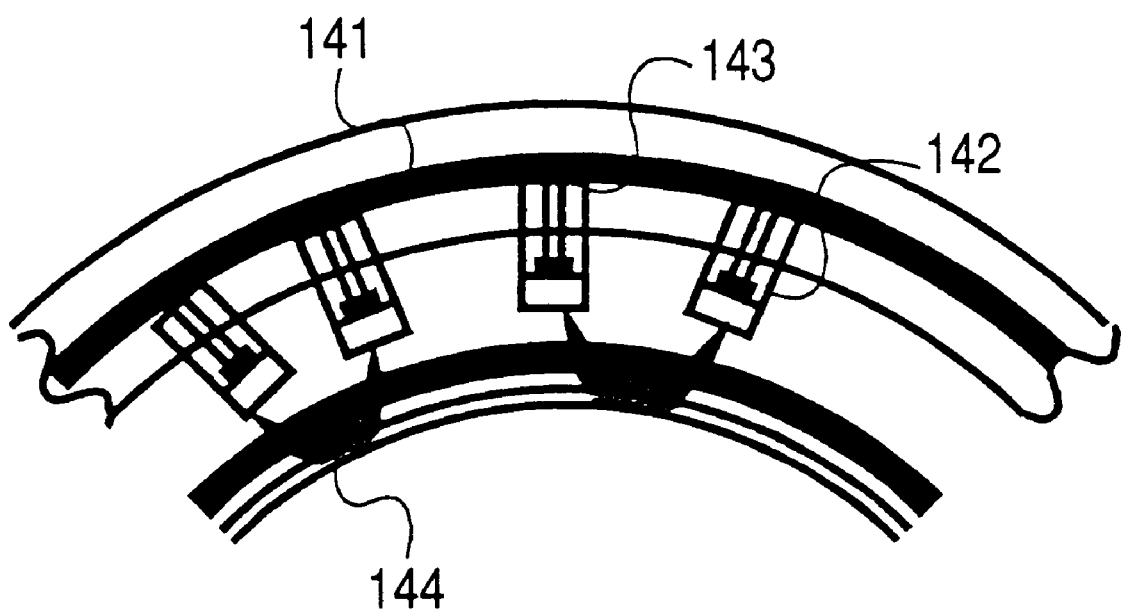
FIG. 14 shows an embodiment of the structure of an electric/electronic circuit within the Katyusha.

FIG. 14 shows an embodiment of the structure of electronic circuit provided within the "Katyusha". For transmission of an electric signal from the power source to the light source and light detector, an electric circuit (141) which can change its shape in flexible is used. Two illuminators (142) and two detectors (143) are respectively used within the "Katyusha" shown in this embodiment. The number of these elements can be set freely. The end part of the "Katyusha" is in contact with the scalp.

Figure 15:
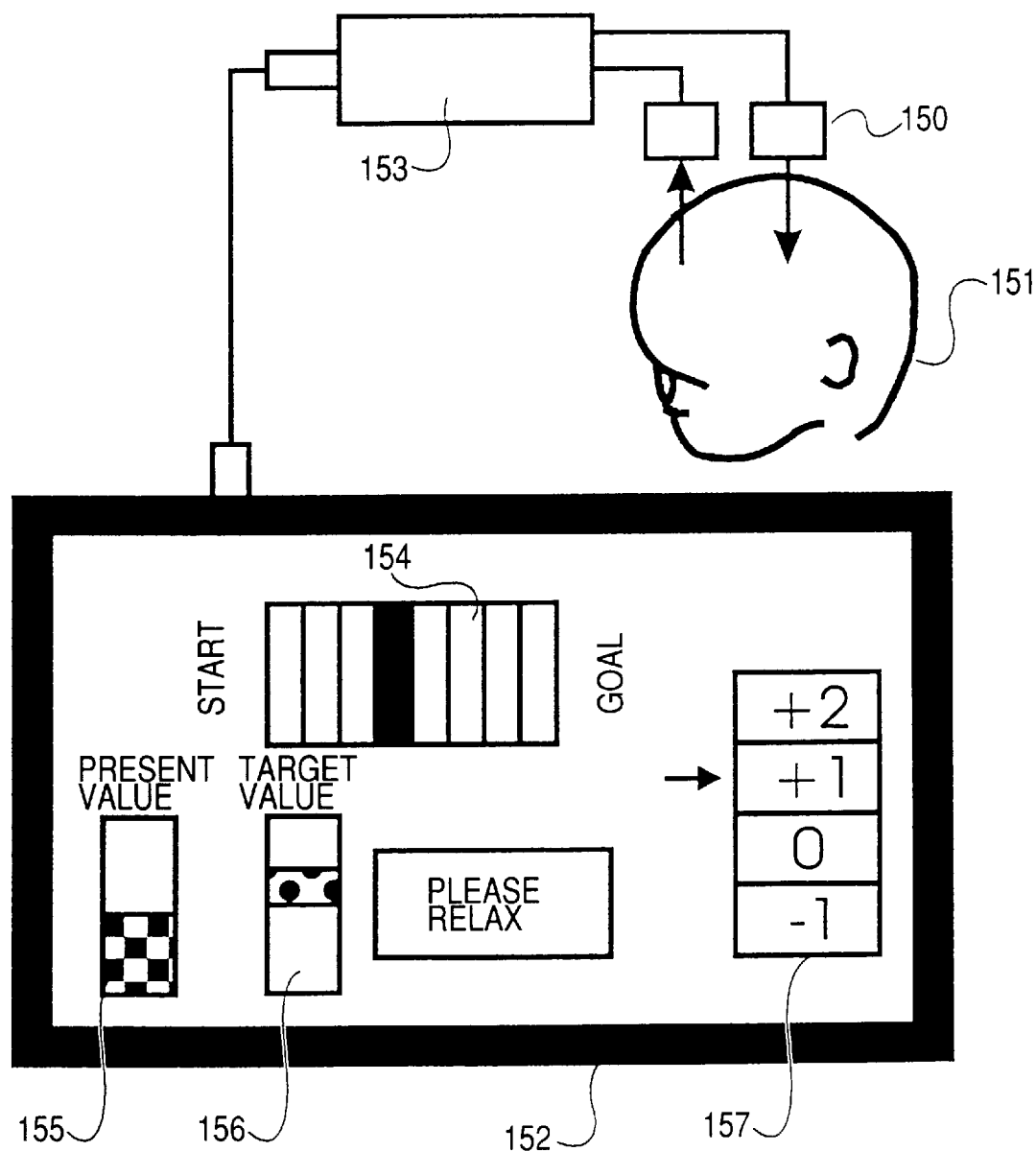
FIG. 15 shows an embodiment of a device for playing games.

Embodiment 6:

FIG. 15 shows an embodiment of a game "Sugoroku" using the means explained above. A player (151) loading a light source and a light detector (150) watches a display (152). The light detector (150) is connected to the display (152) via a signal processor (153). On the display, following items are displayed. Firstly, a display array (154) indicating the position of a step exists. In the case of this embodiment, the nine display areas in total exist between the start and the goal. On the figure of this embodiment, the 4-th area counted from the left side is inverted to the color black. This inverted area suggests that the step exists in this area. The "present value" (155) suggests intensity of the detected light in every time. Moreover, the "target value" (156) specifies the range of intensity of detected light instructed from a controller. Moreover, a discrete value (157) (indicated as +2, +1, 0, −1 in the figure) suggests the number of steps which may be proceeded depending on the detected light intensity.

Figure 16:
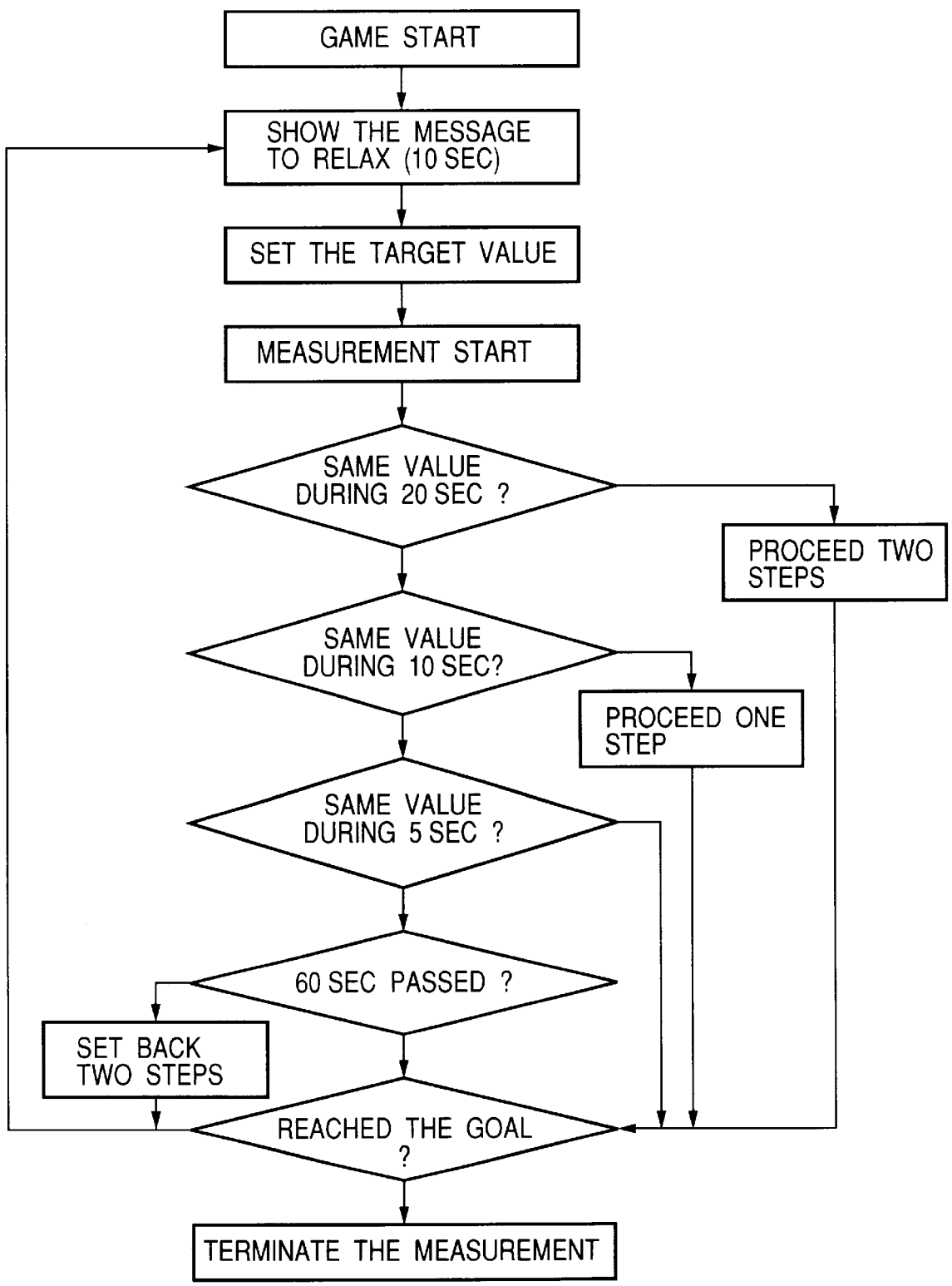
FIG. 16 shows a way of proceeding the Sugoroku game.

A way of progressing this game will be explained with reference to FIG. 16. Firstly, the game can be started when a message is displayed a player to relax. For example, a player is requested to keep quiet for 10 seconds. Next, a target value is set. The target value is set within a certain range. This target value may be set freely. As an example, this target value is determined using a random number. Next, a message indicating the start of measurement is displayed on the display screen and the measurement is started. Here, a player executes, for example, the exercise of hand as shown in FIG. 3 to control the detected light intensity. The detected light intensity is displayed on the bar as the value of the "present value". When this "present value" stays for 20 seconds or 10 seconds within the "target value" having a certain range, the two steps and one step can be attained, respectively. Moreover, if the "present value" depending on the time stays only for 5 seconds or less among the value of "target value" even after the measurement for 60 seconds, the two steps are set back. Finally, when the step has reached the goal, the game is over but if the step does not reach the goal, the game should be continued. The time (seconds) indicated in this embodiment is only an example and such time may be set freely for every player of the game. A program describing the way of putting forward the game is shown in FIG. 10, for example, when the structure of device shown in FIG. 10 is introduced.

The signal processing system is stored in the fixed disc 107 and memory 108 and is then controlled with the CPU 100. Moreover, in the fixed disc 107 and memory 108, the information pieces which are required for proceeding the game represented by the "present value" (155), "target value" (156) and "discrete value" (157) are stored.

Figure 17:
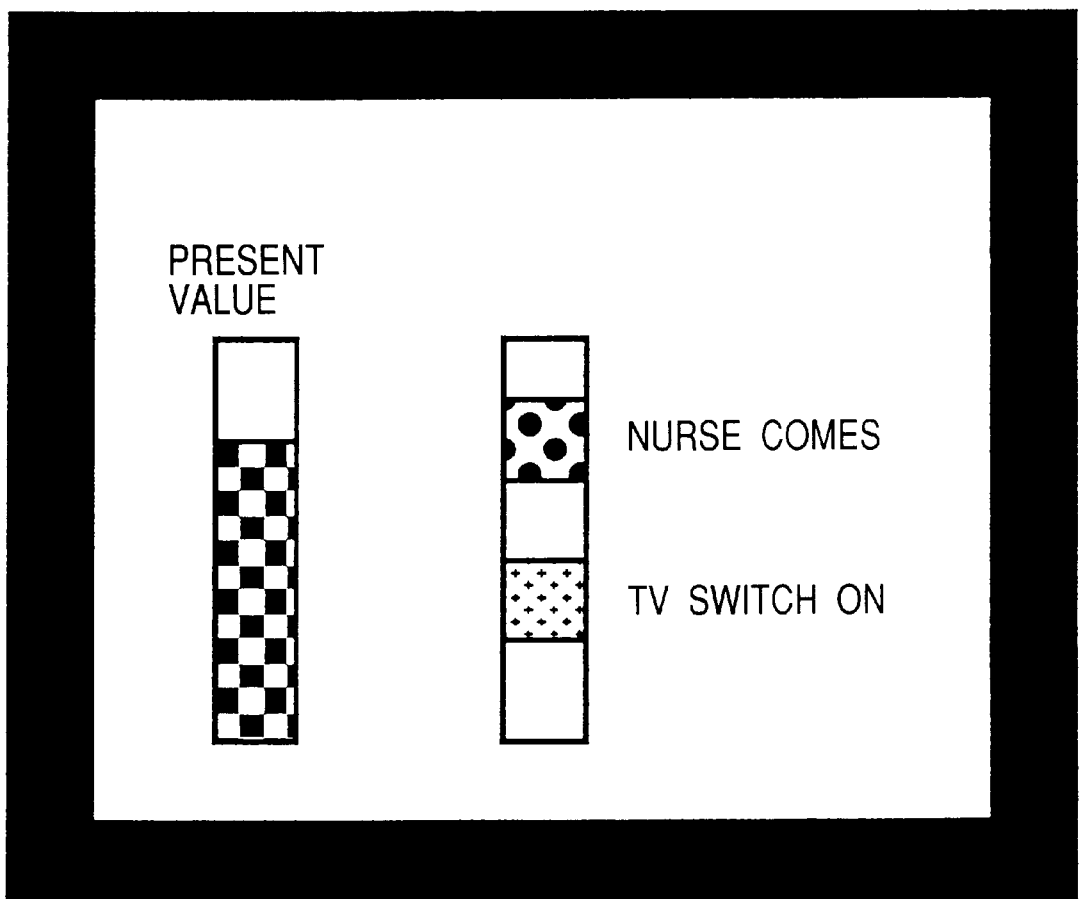
FIG. 17 shows an example of application within a hospital room.

Embodiment 7:

FIG. 17 shows an example of the use in the hospital room as the application example of the optical measuring instrument of FIG. 1. In this embodiment, one optical measuring instrument is capable of realizing a nurse call and turning ON of the switch of the television receiver installed in the hospital room by utilizing the optical measuring instrument shown in FIG. 1. Numeral 171 denotes a display screen wherein a bar for displaying the "present value" of the detected light intensity and the "target value setting bar". In the target value setting bar, the area displaying "A nurse will come" and the area displaying "Turning ON the TV switch" exist independently. A subject or a subject person executes, for example, the exercise of hands for alternately repeating the conditions of gripping and palm of hands shown in FIG. 3 in view of activating the brain. As a result, the detected light intensity changes. If intensity of light propagated the tissue can be fixed for a constant period (for example, 10 seconds) within the area displaying "A nurse will come", a nurse call is generated. Moreover, if the detected light intensity can be fixed to the area displaying "Turning ON the TV switch", the TV switch is turned ON through a relay.

Figure 18:
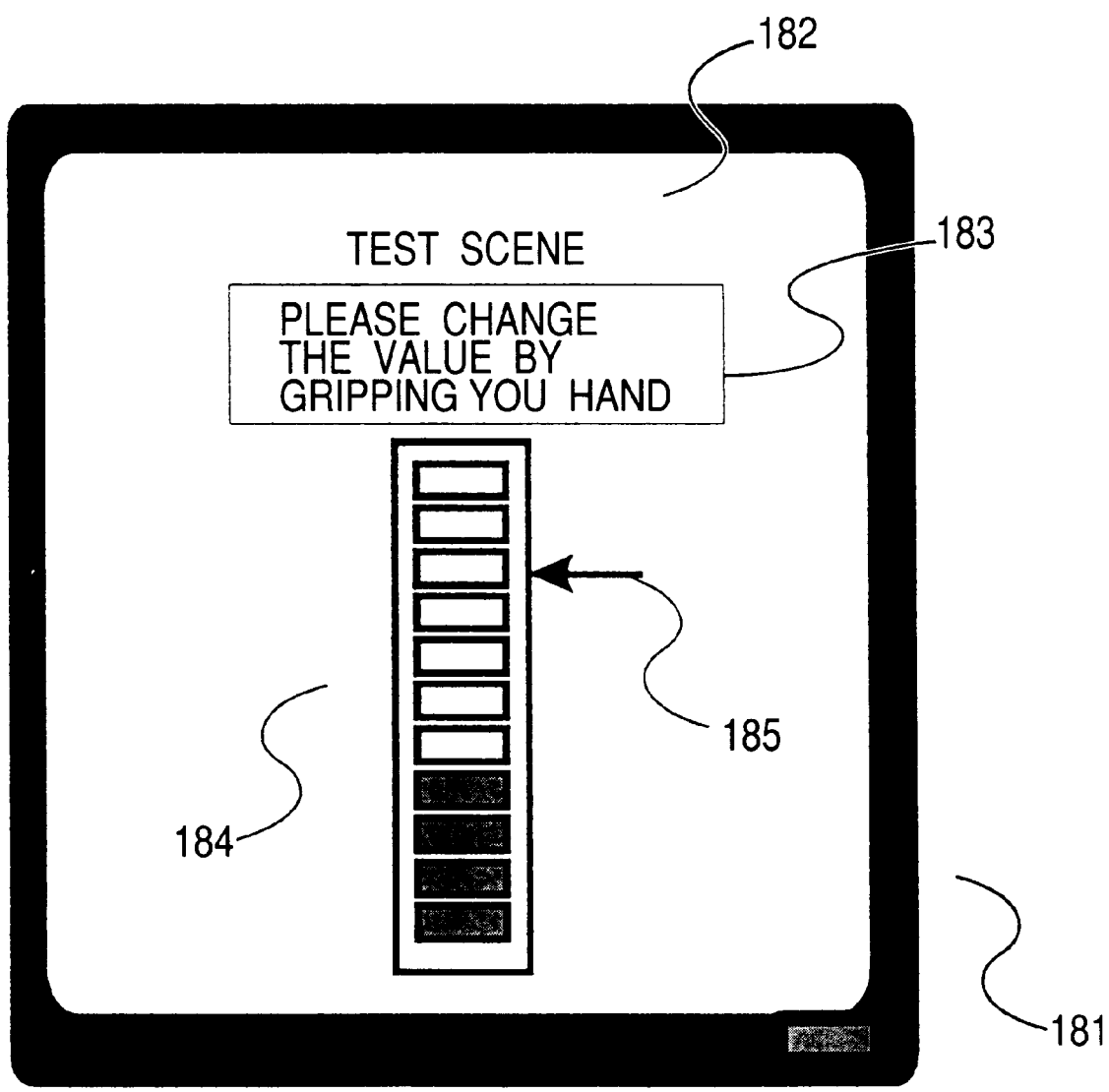
FIG. 18 shows an embodiment of a test scene.

Here, on the occasion of embodying the embodiment of FIG. 1, dependence on time of the detected light intensity is different for every subject or subject person or cerebral function to be activated. Therefore, the subject (player) is requested to detect dependence on time of the detected light intensity before embodying the embodiment of FIG. 15. In order to realize this object, an embodiment of test scene is shown in FIG. 18. In the display (181), a message (182) for presenting the rest scene is presented. Here, the "test" means that the cerebral function is activated and the detected light intensity is changed with a desired means. A message (183) for notifying the start of test is displayed and a measured value (184) is also displayed on the measured value display. Moreover, the target value (185) is displayed. The measured value being displayed is updated in every second.

Figure 19:
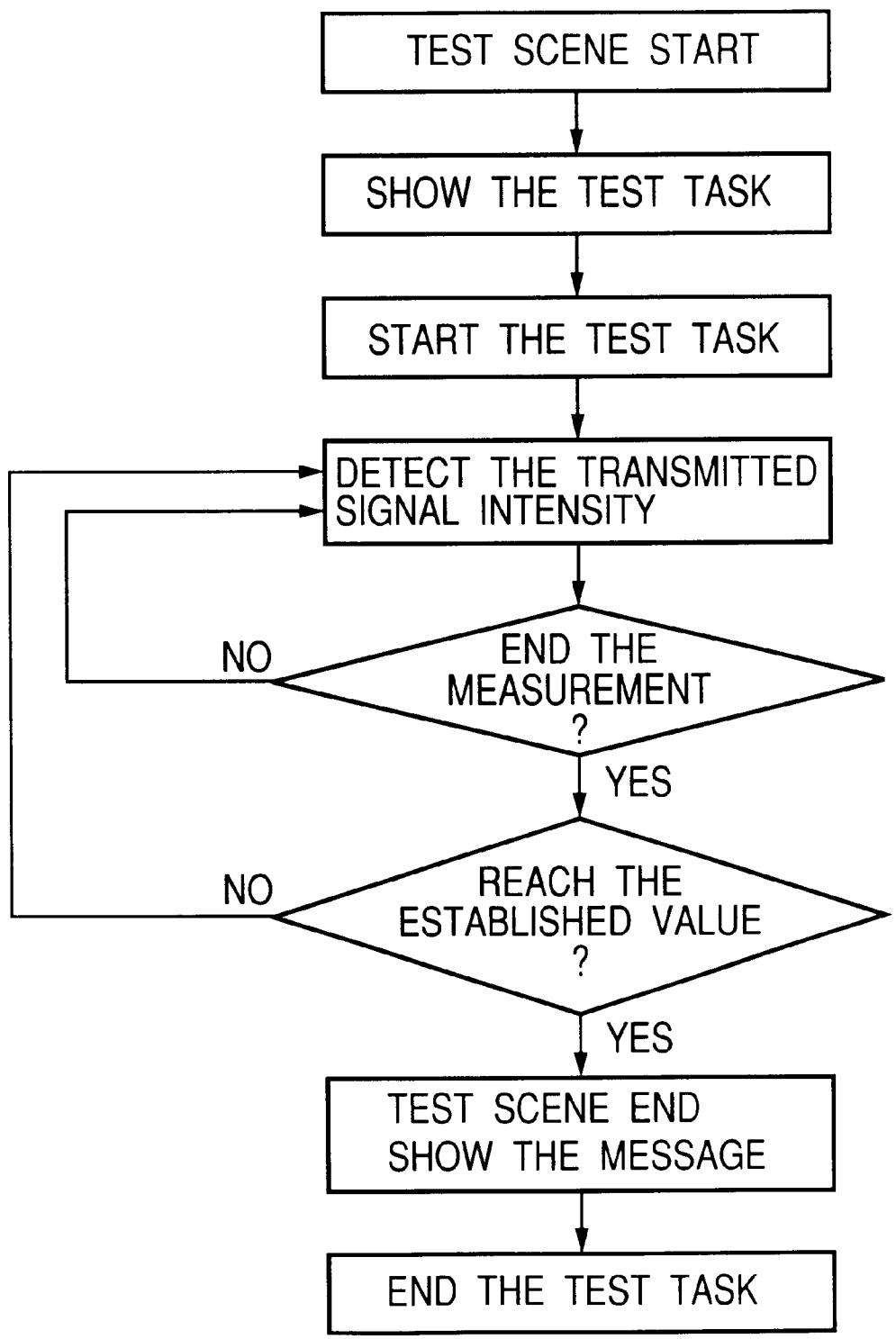
FIG. 19 shows an example of algorithm of FIG. 18.

FIG. 19 shows an embodiment of the target value setting sequence. With start of display of the test scene, start of test can be instructed. In the presentation of the test task, contents of the task to be tested is presented. When an instruction for start of test task, the subject executes the task presented by presentation of test task. With progress of execution of task, intensity of light propagated the tissue is idetected. Information about detected intensity and relative time or absolute time of the detected signal are stored on the memory. The memory used here may be a memory represented by a dynamic RAM (DRAM) which requires the storing and holding operations or may be a swap memory using a fixed disc. When the preset intensity cay be achieved, the measurement is terminated. Moreover, when a constant time has passed (end of the measurement time), the measurement is also terminated. Dependence on time of the signal intensity change obtained during the measurement period can be detected as the intrinsic characteristic of the signal intensity change of individuals. Namely, difference among individuals can be detected. The end of measurement is displayed (end of measurement time) and thereby the display of the test scene is terminated (end of test scene).

Figure 20:
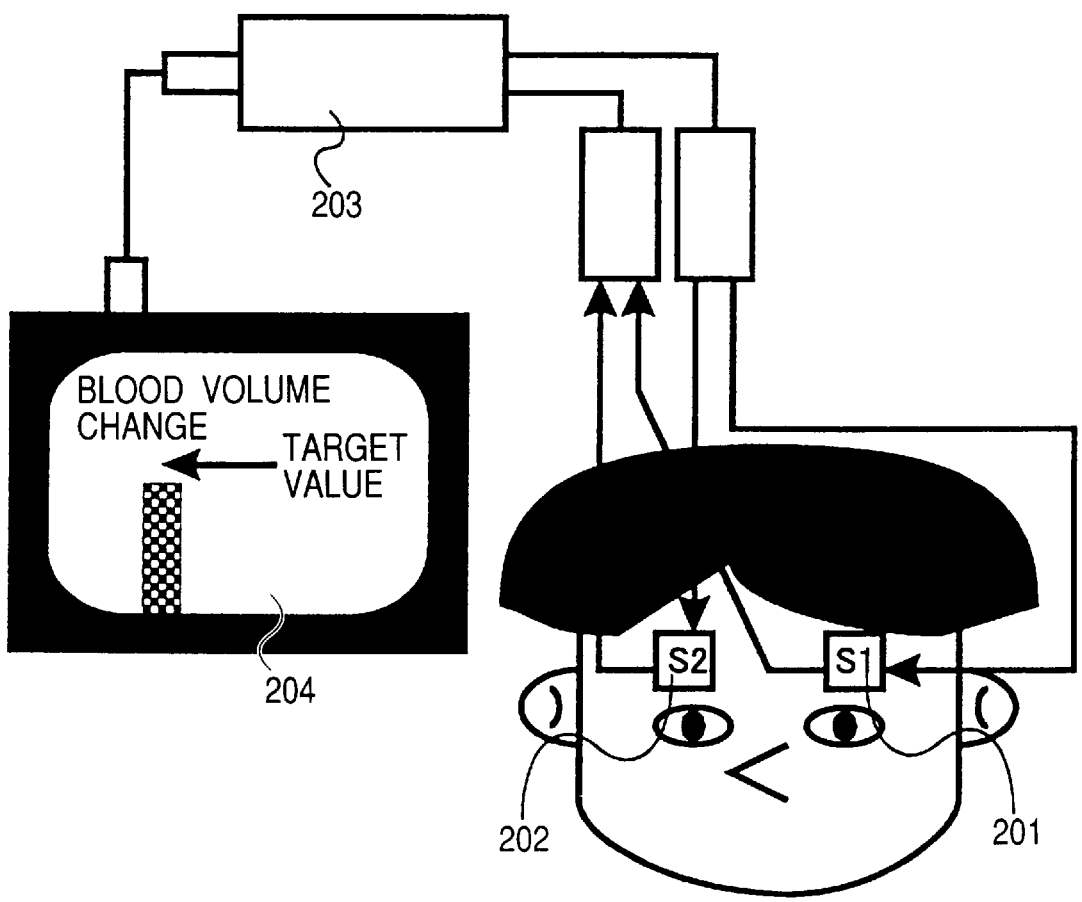
FIG. 20 shows an embodiment of a measuring method in which two light source means are provided.

In FIG. 1, a light source and a light detector are located on the subject. In this case, it is probable that intensity of light transmitted the tissue detected through the motion of body is varied with a cause other than the activity of brain. Therefore, a measuring means which can improve this problem is shown in FIG. 20. As shown in FIG. 20, the light source is provided in the two areas. For example, when the gripping and palm of the hand are repeated (on the occasion of activating the motor area of the right hand), the motor area in left hemisphere is activated. Therefore, the light source and light detector (S1) which can detect such cerebral activity are allocated on the motor area in left hemisphere (201). Meanwhile, the similar light source and light detector are also allocated (S2) also at the area (motor area in right hemisphere) symmetrical to such allocation area about the center (202). The signal processor (203) calculates a difference between S1 and S2 and then transmits the result to the image display (204). In this display (204), this difference value is displayed.

Figure 21:
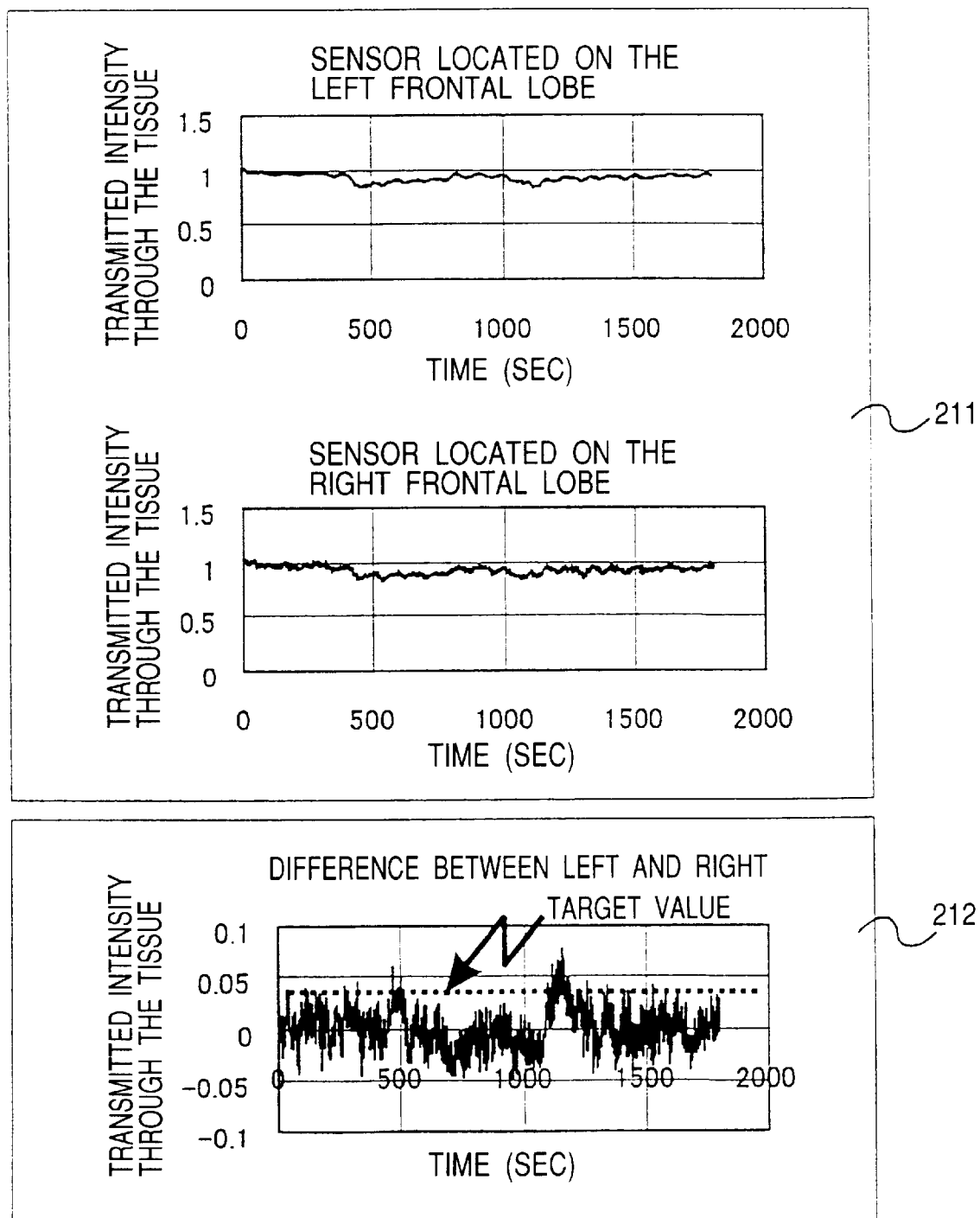
FIG. 21 shows an embodiment of the measuring method shown in FIG. 20.

FIG. 21 shows a result (211) of signal intensity change in right and left hemispheres and a result (212) of difference in signal intensity change between right left hemispheres. In the result (211), it can be understood, as a result of comparison between the transmitted intensity through the tissue detected with a sensor located on the motor area of left hemisphere and the transmitted intensity through the tissue detected with a sensor located on the motor area of right hemisphere, that the transmitted intensity through the tissue in the left hemisphere is large, reflecting the activity of brain. However, when the head moves during the measurement, variation of detected light due to this movement can also be detected. Therefore, signal intensities in the right and left hemispheres are differentiated to individually detect variations of blood volume due to the activity of brain by detecting a variation of detected light and then subtracting such difference. The result 212 is also shown in FIG. 21. Thereby, change of blood volume due to the activity of brain can be extracted by eliminating noise represented with the motion of body.

Figure 22:
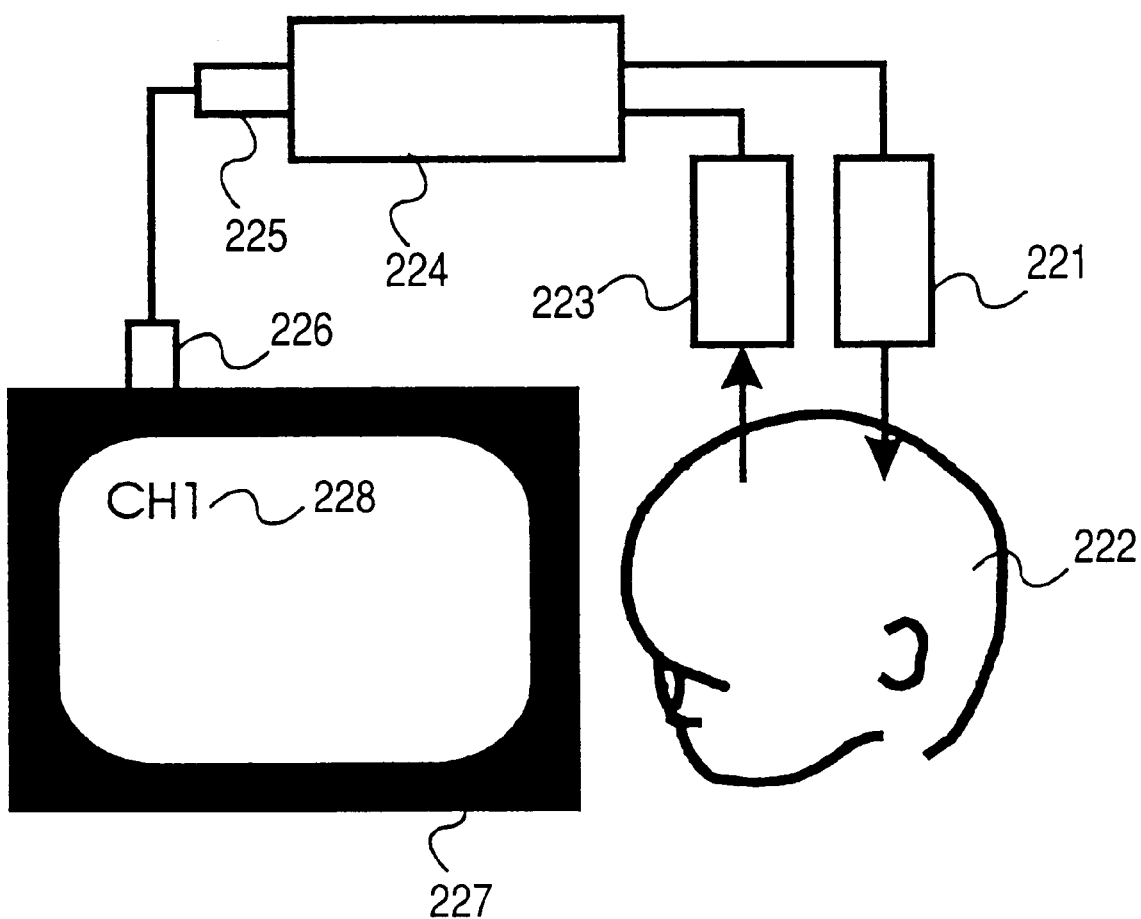
FIG. 22 shows a structure of a volition induction apparatus and an input/output apparatus using an optical measuring instrument and a recording medium.

FIG. 22 shows embodiments of the volition induction apparatus and input/output apparatus using the optical measuring instrument of the present invention and the recording medium. The light source 221 used for measurement is placed in contact on the skin of subject 222. The light source 221 is composed of a light source represented by a semiconductor laser, gas laser, free electron laser, lamp, fluorescent lamp and light emitting diode and an optical wave guide represented by an optical fiber. However, the light source using the light source element represented by a semiconductor laser, gas laser, free electron laser, lamp and light emitting diode may also introduce the structure to be in contact on the subject. The light detector 223 uses an element represented by a photodiode and a photo electron multiplying tube which can detect the light propagated through the tissue. Here, it is also possible to introduce the structure that the light detector represented by such element is located on the skin of body or the structure that an optical wave guide is provided between the skin of the body and light detector using an optical guiding means as in the case of the light source 221. The light source 221 and the light detector 223 are connected to the signal processor 224. The detected signal intensity is transmitted to a television receiver 227 via the signal output connector 225 and signal input connector 226. On this television display, a channel (228) is displayed (display of "CH1" in the figure). The subject activates the activity of brain by moving, for example, hand and leg and also assuming a something. When the brain is activated, the blood volume in the brain changes and therefore intensity of light detected with the light detector 223 also changes. For example, it is assumed here that detected light intensity before activity of brain is 1, the blood volume increases due to the activity of brain and detected signal intensity is reduced as a result. When the detected light intensity is for example 0.7 or less, the signal processor 224 switches the channel of television receiver to "CH4" from "CH1". With employment of this method, the subject can change the blood volume in the brain by assuming a something and moving the hand and leg. Thereby, the channel of television receiver can be switched as a result.

INDUSTRIAL APPLICABILITY

The present invention explained above provides the following applications as an example. Firstly, it is an input apparatus of computer represented by a game machine. An input apparatus represented by a joy-stick and mouse has been used in the game machine of the related art. This input apparatus requires movement of hands and legs depending on the instruction from the brain. For example, a person having handicaps in the hand or leg cannot utilize these input apparatuses. A volition transmitting means can be assured by utilizing the apparatus provided with the present invention and thereby it is now possible to input the signal to the computer.

Secondly, a person having handicap in the hand or leg can now use such input apparatus. For example, it is assumed there exists a person having handicap in the hand or leg. These persons cannot move their hands or legs if they desire to "move the hand". When the function of the nerves to move the hand of this person is lost and the function of the motor area in the brain is maintained, the motor area can be activated by requesting the action to move the hand. The activating condition of this cerebral function is detected with the light and an artificial hand, in place of the actual hand, can also be controlled depending on the detected volume of light.

What is claimed is:

1. A volition induction apparatus, using an optical measuring instrument, comprising:
    a light source for irradiating a subject of a living body with light;
    a light detector for detecting light signals from a predetermined area of the subject irradiated by said light source;
    a memory for storing the signals detected by said light detector; and
    an input/output display for setting and displaying the present level of the signals obtained from said memory and a predetermined level as a target,
    wherein by feeding back the signals of said input/output display to the subject, the present level of the signals of said input/output display is updated based on the signals from said memory to induce volition of the subject until the target level can be attained.

2. A volition induction apparatus according to claim 1, wherein said input/output display displays the target level and the present level on the same display screen.

* * * * *